(12) United States Patent
Boyden et al.

(10) Patent No.: US 8,875,714 B2
(45) Date of Patent: Nov. 4, 2014

(54) CODED-SEQUENCE ACTIVATION OF SURGICAL IMPLANTS

(75) Inventors: Edward S. Boyden, Cambridge, MA (US); Roderick A. Hyde, Redmond, WA (US); Muriel Y. Ishikawa, Livermore, CA (US); Eric C. Leuthardt, St. Louis, MO (US); Nathan P. Myhrvold, Medina, WA (US); Dennis J. Rivet, St. Louis, MO (US); Michael A. Smith, San Gabriel, CA (US); Thomas A. Weaver, San Mateo, CA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 853 days.

(21) Appl. No.: 11/710,591

(22) Filed: Feb. 22, 2007

(65) Prior Publication Data

US 2008/0208010 A1     Aug. 28, 2008

Related U.S. Application Data

(63) Continuation-in-part of application No. 11/710,592, filed on Feb. 22, 2007.

(51) Int. Cl.
  *A61B 19/00* (2006.01)
  *A61N 1/372* (2006.01)
(52) U.S. Cl.
  CPC ................................. *A61N 1/37217* (2013.01)
  USPC ........................................... 128/899; 600/37

(58) Field of Classification Search
  USPC ................ 128/899; 600/37, 544–545, 29–31; 606/151–158
  See application file for complete search history.

(56) References Cited

U.S. PATENT DOCUMENTS

| | | | |
|---|---|---|---|
| 4,543,955 A | * | 10/1985 | Schroeppel .................. 600/348 |
| 4,850,372 A | | 7/1989 | Ko et al. |
| 5,041,092 A | | 8/1991 | Barwick |
| 5,156,605 A | | 10/1992 | Pursley et al. |
| 5,415,660 A | | 5/1995 | Campbell et al. |
| 5,575,790 A | | 11/1996 | Chen et al. |
| 5,971,984 A | | 10/1999 | Taylor et al. |
| 6,032,677 A | | 3/2000 | Blechman et al. |
| 6,033,412 A | | 3/2000 | Losken et al. |
| 6,063,121 A | | 5/2000 | Xavier et al. |
| 6,164,284 A | * | 12/2000 | Schulman et al. ............ 128/899 |
| 6,383,185 B1 | | 5/2002 | Baumgart |

(Continued)

FOREIGN PATENT DOCUMENTS

| | | |
|---|---|---|
| JP | 2002-248081 A | 9/2002 |
| JP | 2005-501588 A | 1/2005 |

(Continued)

OTHER PUBLICATIONS

"Hydrocephalus, NPH Treatment"; Medtronic.com; bearing a date of 2007; printed on Feb. 20, 2007; pp. 1-2; Medtronic Inc.; located at http://www.medtronic.com/hydrocephalus/nph/nph_subs/nph_treatment.html.

(Continued)

*Primary Examiner* — Catherine B Kuhlman (57) ABSTRACT

Implants responsive to spatiotemporal signal sequences, and methods of operating implants by transmitting spatiotemporal signal sequences.

6 Claims, 4 Drawing Sheets

(56) References Cited

U.S. PATENT DOCUMENTS

| | | | |
|---|---|---|---|
| 6,450,946 B1* | 9/2002 | Forsell | 600/37 |
| 6,486,588 B2* | 11/2002 | Doron et al. | 310/322 |
| 6,706,042 B2 | 3/2004 | Taylor | |
| 6,730,087 B1 | 5/2004 | Butsch | |
| 6,835,207 B2 | 12/2004 | Zacouto et al. | |
| 6,880,085 B1* | 4/2005 | Balczewski et al. | 713/182 |
| 6,940,209 B2 | 9/2005 | Henderson | |
| 7,011,624 B2 | 3/2006 | Forsell | |
| 7,016,735 B2 | 3/2006 | Imran et al. | |
| 7,052,488 B2 | 5/2006 | Uhland | |
| 7,083,650 B2 | 8/2006 | Moskowitz et al. | |
| 7,170,214 B2 | 1/2007 | Henderson et al. | |
| 7,309,943 B2 | 12/2007 | Henderson et al. | |
| 7,339,306 B2 | 3/2008 | Henderson | |
| 7,344,541 B2 | 3/2008 | Haines et al. | |
| 7,559,951 B2 | 7/2009 | DiSilvestro et al. | |
| 2002/0198604 A1 | 12/2002 | Schulman et al. | |
| 2003/0124480 A1 | 7/2003 | Peacock, III | |
| 2003/0130616 A1* | 7/2003 | Steil et al. | 604/66 |
| 2003/0157474 A1 | 8/2003 | Clausen et al. | |
| 2004/0122305 A1 | 6/2004 | Grimm et al. | |
| 2004/0152970 A1 | 8/2004 | Hunter et al. | |
| 2004/0167625 A1 | 8/2004 | Beyar et al. | |
| 2004/0209218 A1 | 10/2004 | Chishti et al. | |
| 2005/0052098 A1 | 3/2005 | Henderson | |
| 2005/0203517 A1 | 9/2005 | Jahng et al. | |
| 2005/0208095 A1 | 9/2005 | Hunter et al. | |
| 2005/0234448 A1 | 10/2005 | McCarthy | |
| 2005/0234555 A1 | 10/2005 | Sutton et al. | |
| 2005/0258714 A1 | 11/2005 | Henderson et al. | |
| 2005/0261769 A1 | 11/2005 | Moskowitz et al. | |
| 2005/0267353 A1* | 12/2005 | Marquart et al. | 600/411 |
| 2006/0036259 A1 | 2/2006 | Carl et al. | |
| 2006/0036323 A1 | 2/2006 | Carl et al. | |
| 2006/0049720 A1 | 3/2006 | Henderson et al. | |
| 2006/0069447 A1 | 3/2006 | DiSilvestro et al. | |
| 2006/0079898 A1 | 4/2006 | Ainsworth et al. | |
| 2006/0136062 A1 | 6/2006 | DiNello et al. | |
| 2006/0173238 A1* | 8/2006 | Starkebaum | 600/37 |
| 2006/0247722 A1 | 11/2006 | Maschino et al. | |
| 2006/0252983 A1 | 11/2006 | Lembo et al. | |
| 2006/0271112 A1 | 11/2006 | Martinson et al. | |
| 2007/0010868 A1 | 1/2007 | Ferren et al. | |
| 2007/0021458 A1 | 1/2007 | Ishikawa et al. | |
| 2007/0156013 A1* | 7/2007 | Birk | 600/37 |
| 2007/0161872 A1 | 7/2007 | Kelly et al. | |
| 2007/0161888 A1 | 7/2007 | Sherman et al. | |
| 2007/0168036 A1 | 7/2007 | Ainsworth et al. | |
| 2007/0169567 A1 | 7/2007 | Schulz et al. | |
| 2007/0179493 A1 | 8/2007 | Kim | |
| 2007/0219561 A1 | 9/2007 | Lavallee et al. | |
| 2007/0250172 A1 | 10/2007 | Moskowitz et al. | |
| 2007/0255286 A1 | 11/2007 | Trieu | |
| 2007/0276378 A1 | 11/2007 | Harrison et al. | |
| 2008/0065225 A1 | 3/2008 | Wasielewski et al. | |
| 2008/0183134 A1 | 7/2008 | Vignery et al. | |
| 2008/0195156 A1 | 8/2008 | Ainsworth et al. | |
| 2008/0254416 A1 | 10/2008 | Claudinon et al. | |
| 2008/0294269 A1* | 11/2008 | Fell | 623/23.48 |
| 2009/0076597 A1 | 3/2009 | Dahlgren et al. | |
| 2009/0187120 A1 | 7/2009 | Nycz | |
| 2010/0070033 A1 | 3/2010 | Doty | |
| 2010/0318116 A1 | 12/2010 | Forsell | |

FOREIGN PATENT DOCUMENTS

| | | |
|---|---|---|
| JP | 2006-218234 A | 8/2006 |
| JP | 2008-504590 A | 2/2008 |
| WO | WO 2005/119610 A1 | 12/2005 |

OTHER PUBLICATIONS

Qian, Haifeng; Loizou, Philipos C.; Dorman, Michael F.; "A Phone-Assistive Device Based on Bluetooth Technology for Cochlear Implant Users"; IEEE Transactions on Neural Systems and Rehabilitation Engineering; bearing a date of 2003; pp. 282-287; IEEE.

Squiggle Motors; New Scale Technologies, Inc.; pp. 1-4; located at www.newscaletech.com.

Squiggle motors—miniature piezo motors; New Scale Technologies, Inc.; pp. 1-4; downloaded on Oct. 17, 2008; located at http://www.newscaletech.com/squiggle_overview.html.

Useful Articles and Papers; New Scale Technologies, Inc.; p. 1; downloaded on Oct. 23, 2008; located at http://www.newscaletech.com/article_papers.html#HearingAidPaper.

Analog Devices, Inc., "Small, Low Power, 3-Axis ±3 g iMEMS® Accelerometer—ADXL330"; bearing a date of 2006; pp. 1-16; Analog Devices, Inc., Norwood, MA.

PCT International Search Report; International App. No. PCT/US 10/01119; bearing a date of Jun. 17, 2010; pp. 1-2.

Judy et al.; "A Linear Piezoelectric Stepper Motor With Submicrometer Step Size and Centimeter Travel Range"; IEEE Transactions on Ultrasonics, Ferroelectrics, and Frequency Control; bearing a date of Sep. 1990; pp. 428-437; vol. 37, No. 5; IEEE.

Japanese Office Action; App. No. 2009-550890 (Based on PCT/US2008/002011); pp. 1-2.

UK Intellectual Property Office Combined Search and Examination Report Under Section 17 & 18(3); App. No. GB1109072.7; bearing a date of Sep. 22, 2011; pp. 1-3.

UK Intellectual Property Office Examination Report Under Section 18(3); App. No. GB0916445.0; Jan. 4, 2011; pp. 1-2.

* cited by examiner

CODED-SEQUENCE ACTIVATION OF SURGICAL IMPLANTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/710,592, entitled CODED-SEQUENCE ACTIVATION OF SURGICAL IMPLANTS, naming Edward S. Boyden, Roderick A. Hyde, Muriel Y. Ishikawa, Eric C. Leuthardt, Nathan P. Myhrvold, Dennis J. Rivet, Michael A. Smith, Thomas A. Weaver, and Lowell L. Wood, Jr. as inventors, filed 22 Feb. 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a device for implantation in a body includes a receiver responsive to a selected spatiotemporal signal sequence to produce an activation signal and a member responsive to the activation signal to shift from a first mechanical configuration to a second mechanical configuration. The selected spatiotemporal signal sequence may include spatially separated and/or temporally separated signals, which may include, for example, magnetic fields, electric fields, acoustic signals, electromagnetic signals, and/or optical signals. The member may be configured to engage one or more vertebrae (e.g., a spinal screw), and the second mechanical configuration may provide more or less stress shielding to the vertebrae than the first mechanical configuration. The member may be configured to engage a bony structure (e.g., a tooth), and the second mechanical configuration may provide more or less stress shielding to the bony structure than the first mechanical configuration. The member may include a tissue expander, an intralumenal device (e.g., a stent such as an expandable stent, or a lumen-traversing device including a physiological sensor such as a gastrointestinal camera), a shunt (e.g., a cerebrospinal fluid shunt or a vascular conduit), a drug reservoir (e.g., a reservoir that is configured to dispense a drug by shifting from the first to the second mechanical configuration), an artificial joint, a gastric band, an artificial sphincter, an orthodontic appliance, or a cosmetic implant (e.g., a lip, breast, pectoral, or deltoid augment). The member may be configured to accommodate growth of the body.

In another aspect, a device for providing a coded signal to an implant in a body includes a plurality of signaling units having a selected spatial arrangement. The signaling units are arranged to deliver a spatiotemporal signal sequence corresponding to the coded signal. The spatiotemporal signal sequence may include spatially separated and/or temporally separated signals, which may include, for example, magnetic fields, electric fields, acoustic signals, electromagnetic signals, and/or optical signals, and may include at least two different signal modes. The device may be configured to conform to a surface of the body, and/or may be configured to be secured to the body. The device may further include a receiving unit that is configured to receive a signal from the implant, such as a receiver that can receive a signal selected from the group consisting of magnetic fields, electric fields, acoustic signals, electromagnetic signals, and/or optical signals.

In yet another aspect, a method of treating a patient having a surgical implant of a type responsive to a spatiotemporal signal sequence to change from a first mechanical configuration to a second mechanical configuration includes directing a series of signals corresponding to the spatiotemporal sequence into the patient's body. The series of signals may include spatially separated and/or temporally separated signals, which may include, for example, magnetic fields, electric fields, acoustic signals, electromagnetic signals, and/or optical signals. The patient may have a plurality of surgical implants, and fewer than all of the implants (e.g., one implant) may be responsive to the spatiotemporal signal sequence. The method may further include measuring a physiological parameter of the patient (e.g., blood pressure, heart rhythm, breathing rhythm, neurological activity, blood flow, blood oxygenation, end tidal $CO_2$, pressure, viscosity, joint angle, vertebral angle, spinal angle, mechanical stress, shear, torque, distance between selected reference points, mechanical strain, modulus, and/or compressibility), and directing the series of signals in response to the measured physiological parameter. The surgical implant may be configured to engage one or more vertebrae, and the first mechanical configuration may provide more or less stress shielding to the vertebrae than the second mechanical configuration, and/or the implant may change the relative position of the vertebrae. The surgical implant may be configured to engage a bony structure, and the first mechanical configuration may provide more or less stress shielding to the bony structure than the second mechanical configuration. The patient may be a human or an animal, and may be an adult or a juvenile. The surgical implant may be, for example, a tooth implant, a tissue expander, an intralumenal device, a stent, a shunt, a gastrointestinal camera, a drug reservoir, an artificial joint, a gastric band, an artificial sphincter, an orthodontic appliance, a cosmetic implant, a lip augment, a breast augment, a pectoral augment, or a deltoid augment.

In still another aspect, a system for treating a patient includes a signaling unit configured to emit a spatiotemporal signal sequence into the patient, and an implant configured for implantation into the patient. The implant is configured to respond to the spatiotemporal signal sequence by shifting from a first mechanical configuration to a second mechanical configuration. The spatiotemporal signal sequence may include a spatial and/or a temporal arrangement of magnetic fields, electric fields, acoustic signals, electromagnetic signals, and/or optical signals. The implant may be, for example, a bone implant, a spinal implant, a tooth implant, a tissue expander, an intralumenal device, a stent, a shunt, a gastrointestinal camera, a drug reservoir, an artificial joint, a gastric band, an artificial sphincter, an orthodontic appliance, a cosmetic implant, a lip augment, a breast augment, a pectoral augment, or a deltoid augment.

In a still yet another aspect, a device for implantation into a body includes a receiver responsive to a trigger signal, authentication circuitry coupled to the receiver and operative to distinguish an authentic trigger signal from a non-authentic trigger signal and responsive to an authentic trigger signal to generate an actuation signal, and an actuable member coupled to receive the actuation signal and responsive to the actuation signal to change configuration. The device may further include a physiological sensor configured to sense a physiological parameter in the body (e.g., a parameter indicative of an abnormal condition of the body such as loss of consciousness, altered consciousness, abnormal heart rhythm, abnormal breathing rhythm, abnormal blood pressure, abnormal blood chemistry, change in tissue perfusion, myocardial infarction, stroke, hypoglycemia, hyperglycemia, electrolyte disturbance, and/or hormone imbalance), and the authentication circuitry may use the sensed physiological parameter to determine whether to generate an actuation signal (e.g., only if the sensed physiological parameter is indicative of an abnormal condition of the body). The authentication circuitry may be configured to determine that the physiological parameter is indicative of an abnormal condition if it falls outside of a selected normal range, and it may be configured to accept a change in the selected normal range. The receiver may be configured to accept any one of a plurality of trigger signals, each associated with a respective permissions level, and may be configured to generate an actuation signal under different conditions for different permissions levels. The device may be, for example, a bone implant, a spinal implant, a tooth implant, a tissue expander, an intralumenal device, a stent, a shunt, a gastrointestinal camera, a drug reservoir, a pacemaker, a defibrillator, a cochlear implant, a brain stimulator, an artificial joint, a gastric band, an artificial sphincter, an orthodontic appliance, a cosmetic implant, a lip augment, a breast augment, a pectoral augment, or a deltoid augment.

In a further aspect, a device for implantation in a body may include a receiver configured to receive a first signal, a transmitter configured to send a second signal, and an actuable member having a therapeutic function in the body. The actuable member is configured to be actuated after both receipt of the first signal and sending of the second signal. The transmitter may be configured to send the second signal in response to receipt of the first signal by the receiver. Actuation of the actuable member after both receipt of the first signal and sending of the second signal may include actuation in response to a third signal determined by both the first signal and the second signal. The transmitter configured to send the second signal may be a passive transmitter such as an RFID. The second signal may include identifying information for the device. The device may be, for example, a bone implant, a spinal implant, a tooth implant, a tissue expander, an intralumenal device, a stent, a shunt, a gastrointestinal camera, a drug reservoir, a pacemaker, a defibrillator, a cochlear implant, a brain stimulator, an artificial joint, a gastric band, an artificial sphincter, an orthodontic appliance, a cosmetic implant, a lip augment, a breast augment, a pectoral augment, or a deltoid augment.

In yet a further aspect, a method of accessing an implant in a body includes identifying a spatiotemporal signal sequence corresponding to an access code for the implant and providing the identified spatiotemporal signal sequence to the implant without physically contacting the implant. The identified spatiotemporal signal sequence may be a command to the implant, such as a data retrieval command, an actuation command (e.g., to direct the implant to shift from a first to a second mechanical configuration, such as to a configuration that provides a different level of stress shielding to a bony structure), and/or a reconfiguration command (e.g., a command that modifies behavior of a logic circuit in the implant). The command may be a data retrieval command that directs the implant to return a parameter such as implant position, implant shape, implant identity, measurements of a physiological parameter (e.g., blood pressure, heart rhythm, breathing rhythm, neurological activity, blood flow, blood oxygenation, end tidal $CO_2$, pressure, viscosity, joint angle, vertebral angle, spinal angle, mechanical stress, shear, torque, distance between selected reference points, mechanical strain, modulus, and/or compressibility), and/or measurements of an environmental parameter (e.g., temperature, pressure, chemical activity of a substance, chemical concentration of a substance, and acceleration). The implant may be, for example, a bone implant, a spinal implant, a tooth implant, a tissue expander, an intralumenal device, a stent, a shunt, a gastrointestinal camera, a drug reservoir, a pacemaker, a defibrillator, a cochlear implant, a brain stimulator, an artificial joint, a gastric band, an artificial sphincter, an orthodontic appliance, a cosmetic implant, a lip augment, a breast augment, a pectoral augment, or a deltoid augment.

In still a further aspect, a method of accessing an implant in a patient includes receiving identifying information for the patient or for the implant, retrieving implant-specific data corresponding to the identifying information, generating a coded signal responsive to the retrieved implant-specific data, and transmitting the coded signal to the implant. Receiving the identifying information may include interrogating the implant in the patient, and/or accessing a compilation of identifying information. The implant-specific data may include an access code for the implant and/or a location for the implant. Generating the coded signal may include determining a signal operative to induce the implant to shift from a first to a second mechanical configuration, and/or determining a signal operative to induce the implant to transmit information out of the body. The implant may include logic circuitry, and generating the coded signal may include determining a signal operative to induce the implant to modify its logic circuitry.

In yet still a further aspect, a method of operating an implant in the body includes receiving an implant-correlated spatiotemporal signal sequence, and responding to the implant-correlated spatiotemporal signal sequence by performing an action. Responding to the implant-correlated spatiotemporal signal sequence may include determining whether the spatiotemporal signal sequence appears to originate from a sender having permission to actuate the implant. Performing an action may include shifting from a first to a second mechanical configuration, transmitting information out of the body (e.g., a physiological parameter, an environmental parameter, and/or identifying information for the implant), and/or determining a permission level for the implant-correlated spatiotemporal signal sequence. The implant may include logic circuitry that determines response to spatiotemporal signal sequences, and performing an action may also or alternatively include modifying that logic circuitry.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Connection of adjacent vertebrae or other bones via spinal screws (e.g., pedicle screws) or other mechanical structures is common in surgeries such as spinal fusions (which will typically involve removal of one or more intervertebral discs, and, often, filling of the intervertebral space with autologous or exogenous bone, or with a mechanical construct). However, implants may shift in an uncontrolled fashion over time, causing them to become less effective at maintaining alignment. In addition, when the implant structure is too strong, it may provide too much stress shielding to the spine, potentially resulting in bone loss.

Figure 1:
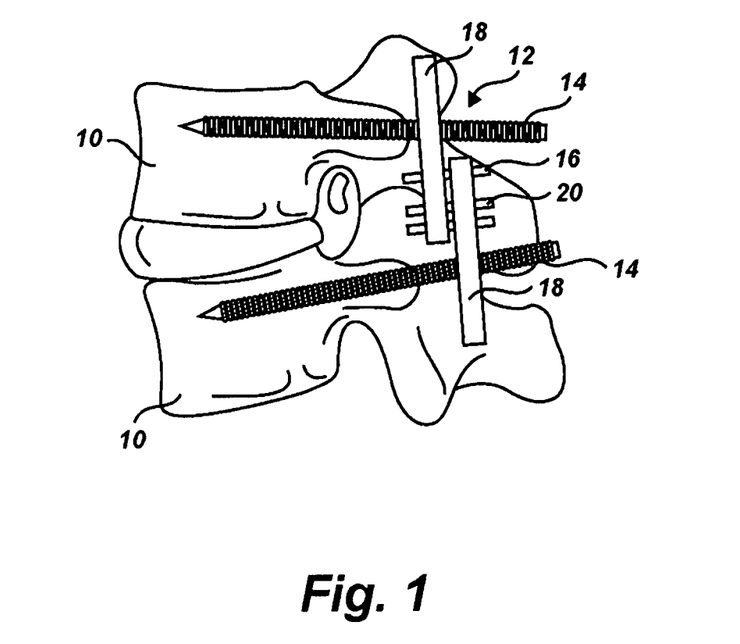
FIG. 1 is a schematic of a spinal implant.

FIG. 1 is a side view of two vertebrae 10 affixed together by means of a spinal implant 12 including pedicle screws 14 and connector 16. Connector 16 has an adjustable length and/or rigidity. Extending the length of connector 16 or increasing its rigidity will generally shift mechanical load from the vertebrae 10 to the implant 12. Connector 16 adjusts its length and/or rigidity in response to a spatiotemporal signal sequence, typically (but not necessarily) received from outside the body. For example, in one embodiment, connector 16 comprises two or more plates 18 connected by one or more pins 20 that may be shifted by application of a spatial pattern of magnetic fields (e.g., an array of magnetic poles having selected polarities), which act as a magnetic "key" for the "lock" of the implant. In the embodiment shown, withdrawal of the pins reduces the rigidity of the implant 12, shifting load to the spine. When the implant is placed in a patient, a doctor may monitor spine healing (e.g., using X-ray, MRI, CT scan, or other diagnostic methods) and remotely adjust the rigidity of the implant in order to facilitate bone regrowth.

Implants responsive to spatiotemporal signal sequences may take a wide variety of forms and respond to a wide variety of signal modes. Spatiotemporal signal sequences may include patterns in time and/or space of electric fields, magnetic fields, electromagnetic fields, acoustic signals, optical signals, or combinations of any of the above. For example, an implant may respond to an acoustic signal followed by a magnetic field (temporal sequence of differing signal modes), a set of magnetic poles in a defined spatial arrangement (spatial sequence of similar signal modes), or a pair of optical signals in a defined spatial arrangement followed by an electric field having defined characteristics (spatiotemporal sequence of differing signal modes). Implant types may include, for example, those that engage bony structures (e.g., the spinal support implant shown in FIG. 1, structures supporting other joints, structures supporting fractures, or structures configured to influence bone growth and/or bone regrowth, such as orthodontic implants or braces for the treatment of scoliosis), tissue expanders, intralumenal devices (e.g., a stent such as an expandable stent, or a device that traverses a lumen such as a gastrointestinal camera), shunts (e.g., a CSF shunt or a vascular conduit), a drug reservoir, a gastric band, an artificial sphincter, or a cosmetic implant (e.g., a lip augment, breast augment, pectoral augment, or deltoid augment). In some embodiments, implants may be configured for use in pediatric patients, and may be configured to shift from a first mechanical configuration to a second mechanical configuration in order to accommodate patient growth.

Figure 2:
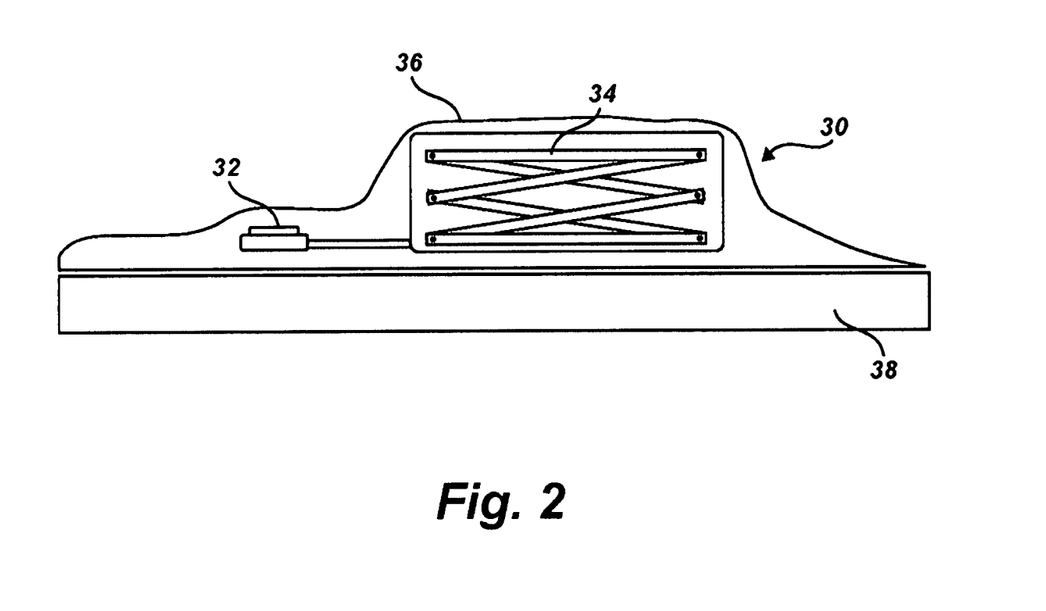
FIG. 2 is a schematic of a tissue expander.

FIG. 2 shows a tissue expander 30 that responds to a spatiotemporal signal sequence. Tissue expanders are commonly used to expand skin in order to graft it from one area of the body to another, and are typically accessed by an injection port, into which a surgeon injects saline periodically over a course of weeks to gradually stretch the skin over the expander. The tissue expander 30 shown in FIG. 2 is configured to expand mechanically, without the need for saline injections, but other configurations may include a saline reservoir. The expander 30 includes a receiver 32 responsive to one or more spatiotemporal signal sequences connected to an expansion member 34 that expands (and/or contracts) in response to signal sequence(s). The expansion member 34 is placed subcutaneously between the skin 36 and underlying muscle 38. As shown, the expansion member 34 includes a mechanical "accordion" style expander, but any other mechanism which can expand the volume of the cavity without unacceptably damaging skin 36 or muscle tissue 38 may be used. In one embodiment (not shown), the expansion member may be a flexible bag which is filled with fluid from a reservoir stored in a body cavity. In such embodiments, fluid may be pumped from the reservoir to the bag (and in some embodiments from the bag to the reservoir). Alternatively, the bag may be filled with a suitable body fluid (e.g., blood serum) which may be naturally replaced by the body.

Figure 3:
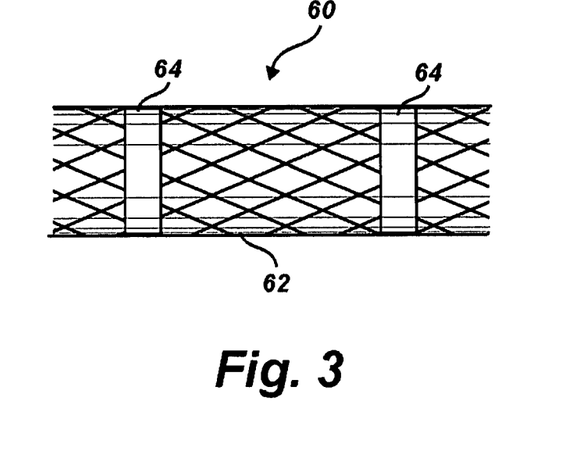
FIG. 3 is a schematic of an expandable stent.

FIG. 3 shows an expandable stent 60. The stent 60 includes a biocompatible wire frame 62 and two actuator rings 64. The actuator rings 64 are configured to expand and/or to contract in response to one or more spatiotemporal signal sequences, and thereby to expand or contract wire frame 62 which forms the body of the stent. The size of the stent can be adjusted after placement in the body by expansion and/or contraction of the rings, either during or immediately after placement (e.g., for initial deployment of the stent), or at a later time (e.g., to further expand a vessel that is becoming clogged without a need for additional surgeries).

Figure 4:
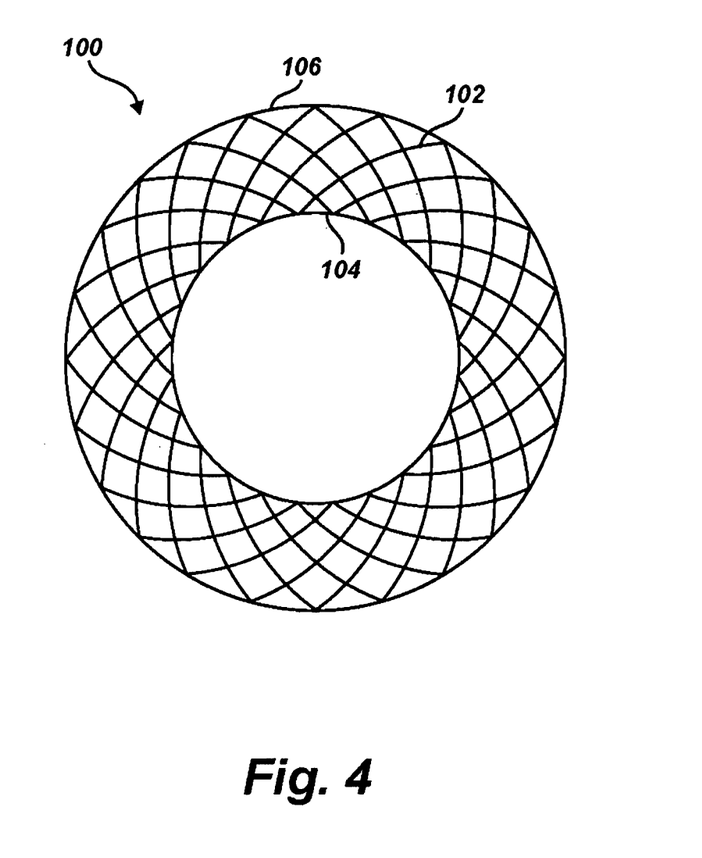
FIG. 4 is a schematic of an artificial sphincter in an expanded state.
Figure 5:
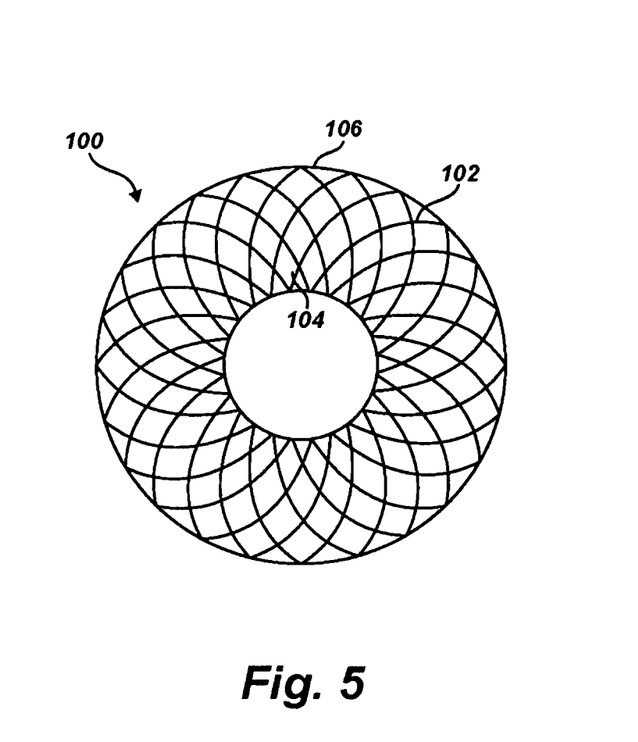
FIG. 5 is a schematic of the artificial sphincter of FIG. 4 in a retracted state.

FIG. 4 and FIG. 5 show an artificial sphincter 100 in expanded and retracted states, respectively. The artificial sphincter may be used, for example, to replace or augment a sphincter muscle such as the esophageal, pyloric, urethral, or anal sphincter. As shown, the artificial sphincter comprises a wire-frame ring structure 102, a movable inner ring 104, and a fixed outer ring 106. In some embodiments, the inner ring 104 contracts and/or expands in response to a coded signal, and the wire-frame elements 102 rotate in response, while in other embodiments, the wire-frame elements actively move in response to the coded signal. For example, the inner ring 104 or the wire-frame elements 102 may include memory alloys, piezoelectric elements, magnetostrictive elements, memory polymers, or other active materials that respond to a spatiotemporal signal sequence. In some embodiments, different portions of the sphincter 100 may comprises different ones of these materials, so that a combination of signals is required to actuate the sphincter. The sphincter 100 may further circuitry (not shown) for processing the coded input signal to determine its mechanical response. For example, the sphincter may include authentication circuitry that processes received signals to determine that they originate from an authorized user. This authentication circuitry may help ensure that the sphincter can only be opened or closed by the patient and/or his doctor. For example, a replacement urethral or anal sphincter may be configured to be opened in response to a spatiotemporal signal sequence received from the patient (e.g., including a patient-specific code), allowing the patient to relieve himself appropriately, but not allowing an inadvertently received signal (e.g., from another patient with a similar implant) to open the sphincter.

A wide variety of other implants may be actuated by means of spatiotemporal signal sequences. For example, some surgical weight loss treatments involve artificially constricting the stomach to deter overeating. In one embodiment, a gastric band or other bariatric implant may be adjusted via a spatiotemporal signal sequence (e.g., gradually loosening the band as the patient develops better eating habits). In another embodiment, an intralumenal device (e.g., a gastrointestinal camera) may be remotely controlled, for example to change the data rate or residence time when the camera passes through an area of interest. In a further embodiment, a shunt may be remotely adjustable (e.g., a CSF shunt may be adjusted via a spatiotemporal signal sequence to adjust the pressure of spinal fluid, or a vascular conduit may be adjusted in a pediatric patient to accommodate growth). In another embodiment, a drug reservoir may shift its mechanical configuration to dispense a drug in response to a signal sequence. In yet another embodiment, an orthodontic appliance (e.g., braces or a retainer) may be responsive to a signal sequence. In still another embodiment, a cosmetic implant (e.g., an augment for the lip, breast, pectoral muscle, or deltoid muscle) may respond to the signal sequence. For example, a breast implant could be gradually increased in size over a period of many days, allowing the skin to stretch gradually as described above in connection with the tissue expander. Cosmetic implants may also be configured for long-term reshaping, for example in response to social norms as an individual ages and/or moves from one social community to another.

In some embodiments, the implant may be partially placed under patient control. For example, for an orthodontic appliance, a progressive, stepwise shifting of the teeth may be accomplished by providing a patient with a signaling device and instructing him to actuate it when the teeth no longer ache from the previous shift. Similarly, a patient may be given (possibly limited) control over a gastric band, controlling the rate of a gradual loosening of the band.

Figure 6:
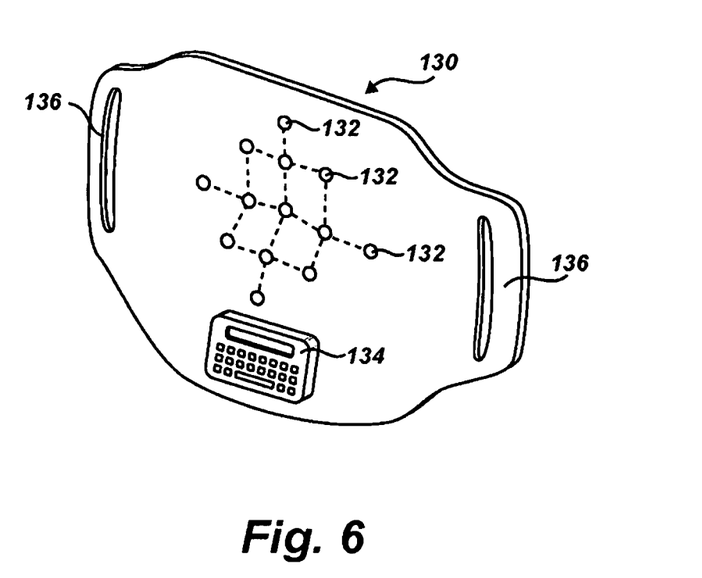
FIG. 6 is a schematic of a signaling device.

FIG. 6 shows a signaling device 130 for providing a coded signal to an implant in the body. As shown, the device 130 includes thirteen magnetic signaling units 132, each configured to create a magnetic field having a selected strength and polarity, but other signaling modalities such as electric fields, electromagnetic signals, acoustic signals, or optical signals may also be used. A controller 134 at the base of the device allows the user to select a desired polarity and/or field strength for each signaling unit 132. In embodiments with selectable polarity, the selection may be between two opposing polarities, or it may include the possibility of additional angles. For example, in some embodiments (not shown), the magnetic signaling units 132 may be configured to be rotated, either automatically or manually.

In some embodiments, a handle (not shown) may be provided, or the device may include straps or other apparatus for securing the device to a body (e.g., the slots 136 for straps shown in FIG. 6). While in the illustrated embodiment, controller 134 is integrated with the signaling device 130, in other embodiments the controller may be separate, either connected by a cable to communicate with the device 130, or via a wireless connection. For example, in some embodiments (not shown), the signaling device 130 may be responsive to BLUETOOTH™ signals or to other wireless protocols.

As shown in FIG. 6, the signaling units are configured in a fixed geometry relative to one another which is selected to match the geometry of an implant (in some embodiments, not all of the magnetic signaling units 132 will correspond to the geometry of any given implant; for example, implants may be provided in multiple sizes or shapes, wherein different subsets of the magnetic signaling units 132 will correspond to different implant sizes or shapes). In other embodiments, the relative positioning of the signaling units 132 may also be adjusted. As shown, the signaling device 130 is constructed to conform to the contours of a human back, but in other embodiments it may be arranged to conform to other areas of the human body. The device may also include straps, adhesive, or other devices (not shown) for securing the device to a body (for example, for embodiments in which a prolonged communication between the signaling device and an implant is contemplated). In the embodiment shown, the signaling device also includes an optional receiving unit 138, which may be configured to receive any of a variety of possible signals from an implant in the body. For example, the received signal may be an authentication signal that confirms that the user of the signaling device 130 is authorized to command the implant, or it may be a locator signal that allows the user to determine whether the signaling device 130 is correctly positioned relative to the implant.

In some embodiments, an implant also may include authentication circuitry. The authentication circuitry may be configured to determine the authenticity of a received trigger signal, and to actuate the implant only if the received signal is determined to be authentic. For example, an implant may require a code from the patient before it can be actuated, so that it cannot be actuated without the patient's consent. In other embodiments, the implant may require a code from a doctor (instead of or in addition to a code from the patient) in order to actuate the implant. For example, a pacemaker may be adjustable on a temporary basis by the patient (e.g., in anticipation of athletic activity), but may be semi-permanently adjusted by the doctor for therapeutic reasons. Similarly, a patient may be able to make limited short-term adjustments to a cochlear implant in order to respond to unusual ambient noises, while his audiologist may make other types of adjustments to the response of the implant to fit it to the patient's auditory profile.

The authentication circuitry may further use a sensed physiological parameter (e.g., loss of consciousness, altered consciousness, abnormal heart rhythm, abnormal breathing rhythm, abnormal blood pressure, abnormal blood chemistry, change in tissue perfusion, myocardial infarction, stroke, hypoglycemia, hyperglycemia, electrolyte disturbance, and/or hormone imbalance) to determine whether to send an actuation signal (e.g., to send an actuation signal only during an abnormal condition of the body). For example, an implanted defibrillator may be configured to be actuated only when an authentic signal is received and when the patient exhibits an abnormal heart rhythm. In some embodiments, the authentication circuitry may be configurable, either before or after implantation into a patient. For example, the circuitry may be configured to accept a range of blood pressures that can be considered to be normal for a particular patient. In some embodiments, this range can be adjusted after the implant has been placed.

The sensed physiological parameter may also be used to alter the permissions required to actuate the implant. For example, an implanted defibrillator may require codes from both doctor and patient for actuation when patient's sensed heart rhythm appears to be normal (or may not be actuatable at all during normal heart rhythm), may be actuated by the patient or the doctor when the heart appears to be beating with an abnormal rhythm, and may be actuated by anyone when the heart has stopped beating.

In embodiments in which the implant senses a physiological parameter and/or an environmental parameter (e.g., temperature, pressure, chemical activity and/or concentration of a substance, and/or acceleration), the implant may be configured to transmit such information in response to an authentication signal. The implant may be configured to transmit either instantaneous values of the parameter, and/or a historical record of past values of the parameter.

Figure 7:
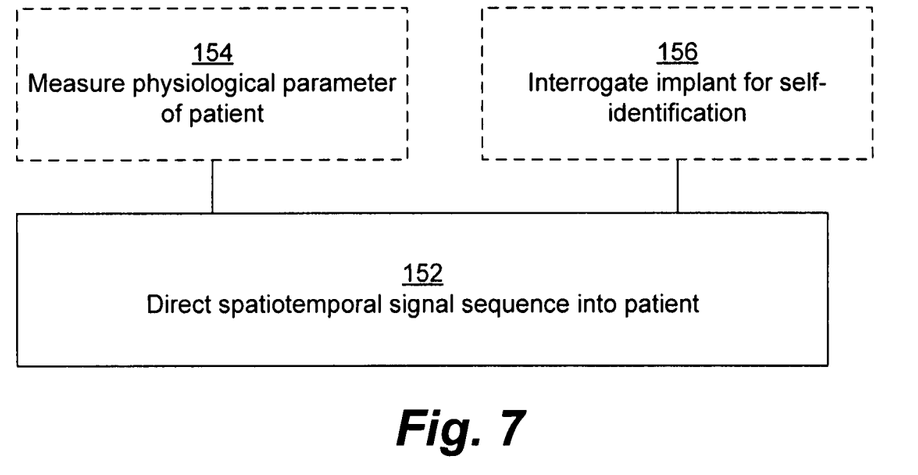
FIG. 7 is a flow chart illustrating a method of treating a patient.

FIG. 7 is a flow chart illustrating a method of treating a patient having a surgical implant of a type responsive to a spatiotemporal signal sequence to change from a first mechanical configuration to a second mechanical configuration. The method includes directing 152 a series of signals corresponding to the spatiotemporal signal sequence into the patient's body. It may also include measuring 154 a physiological parameter of the patient, and directing 152 the series of signals in response to the measured parameter. For example, the method may include monitoring the stress level in a vertebra, and sending a signal sequence to adjust the implant of FIG. 1 in response to the monitored stress, or monitoring blood chemistry and adjusting an expandable stent in response to the monitored chemistry. Other monitored physiological parameters may include, for instance, blood pressure, heart rhythm, breathing rhythm, neurological activity, blood flow, blood oxygenation, end tidal $CO_2$, pressure, viscosity, joint angle, vertebral angle, spinal angle, mechanical stress, shear, torque, distance between selected reference points, mechanical strain, modulus, or compressibility.

The patient to be treated according to the method illustrated in FIG. 7 may have multiple implants that are responsive to spatiotemporal signal sequences. Directing 152 the series of signals into the patient's body may include directing a signal sequence to which fewer than all such implants will respond, for example directing a signal to which only a single implant will respond. The method may also include interrogating 156 the implant(s) for self-identification. Implants may include an active transmitter and/or a passive self-identification component (such as an RFID), which may convey information about the identity of the implant, such as location, size, shape, serial numbers, and/or information about the types of signals that may be used to actuate the implant.

Figure 8:
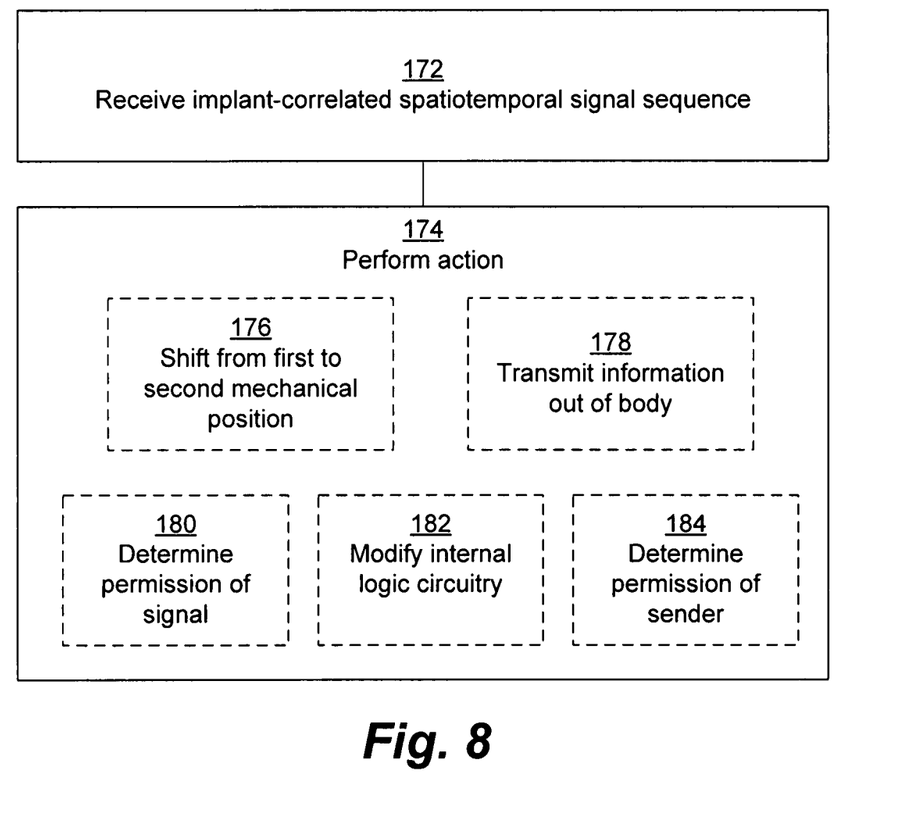
FIG. 8 is a flow chart illustrating a method of operating an implant in a body.

FIG. 8 is a flow chart illustrating a method of operating an implant in a body. The method includes receiving 172 an implant-correlated spatiotemporal signal sequence, and responding 174 to the received signal sequence by performing an action. Some examples of actions may be shifting 176 from a first to a second mechanical position in the body, transmitting 178 information out of the body (e.g., a physiological parameter, an environmental parameter, and/or identifying information for the implant), determining 180 a permission level for the implant-correlated signal sequence, or modifying 182 internal logic circuitry that determines response to spatiotemporal signal sequences (e.g., changing a "normal" range of a physiological parameter, and/or adding an authorized user). Responding may also include determining 184 whether the spatiotemporal signal sequence appears to originate from a sender having permission to actuate the implant.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device for implantation in a body, comprising:
a receiver responsive to a trigger signal;
authentication circuitry coupled to the receiver and operative to distinguish an authentic trigger signal from a non-authentic trigger signal, the authentication circuitry being responsive to an authentic trigger signal to generate an actuation signal;
an actuatable member coupled to receive the actuation signal, the actuatable member being responsive to the actuation signal to change configuration; and
a physiological sensor configured to sense a physiological parameter in the body,
wherein the receiver is configured to accept any one of a plurality of trigger signals, each trigger signal being associated with a respective permissions level, and wherein the authentication circuitry is operative to use the sensed physiological parameter together with the permissions level to distinguish an authentic trigger signal from a non-authentic trigger signal.

2. The device of claim 1, wherein the authentication circuitry is configured to generate an actuation signal after receiving the trigger signal only if the sensed physiological parameter is indicative of an abnormal condition of the body.

3. The device of claim 2, wherein the abnormal condition of the body is selected from the group consisting of loss of consciousness, altered consciousness, abnormal heart rhythm, abnormal breathing rhythm, abnormal blood pressure, abnormal blood chemistry, change in tissue perfusion, myocardial infarction, stroke, hypoglycemia, hyperglycemia, electrolyte disturbance, and hormone imbalance.

4. The device of claim 2, wherein the authentication circuitry is configured to determine that the physiological parameter is indicative of an abnormal condition if the physiological parameter falls outside of a selected normal range.

5. The device of claim 4, wherein the authentication circuitry is configured to accept a change in the selected normal range.

6. The device of claim 1, wherein the device is selected from the group consisting of a bone implant, a spinal implant, a tooth implant, a tissue expander, an intralumenal device, a stent, a shunt, a gastrointestinal camera, a drug reservoir, a pacemaker, a defibrillator, a cochlear implant, a brain stimulator, an artificial joint, a gastric band, an artificial sphincter, an orthodontic appliance, a cosmetic implant, a lip augment, a breast augment, a pectoral augment, and a deltoid augment.

* * * * *